United States Patent

Ochsner

[11] 3,935,205
[45] Jan. 27, 1976

[54] DIMORPHOLINOMETHYL-(4-METHYL-3-PENTENYL)-CYCLOHEXENENES

[75] Inventor: Paul Albert Ochsner, Geneva, Switzerland

[73] Assignee: Givaudan Corporation, Clifton, N.J.

[22] Filed: Sept. 3, 1974

[21] Appl. No.: 502,464

[30] Foreign Application Priority Data
Sept. 21, 1973 Switzerland.................. 13606/73

[52] U.S. Cl............. 260/246 B; 260/598; 424/248
[51] Int. Cl.²..................................... C07D 295/08
[58] Field of Search................ 260/246 B, 563 R Primary Examiner—Nicholas S. Rizzo
Assistant Examiner—Jose Tovar
Attorney, Agent, or Firm—Thomas Cifelli, Jr.

[57] ABSTRACT

Compounds of the formula

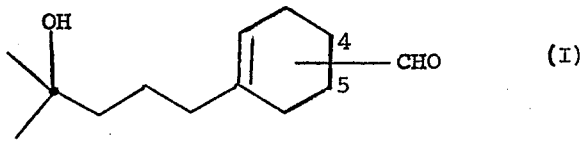

are prepared by hydrating novel compounds of the formula

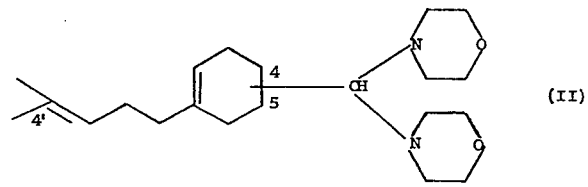

and cleaving off the dimorpholino group.

1 Claim, No Drawings

DIMORPHOLINOMETHYL-(4-METHYL-3-PENTENYL)-CYCLOHEXENENES

FIELD OF THE INVENTION

This invention relates to the field of fragrances (I) and to novel intermediates therefor (II).

SUMMARY OF THE INVENTION

The invention concerns a novel process for the manufacture of aldehydes, namely, compounds of the formula

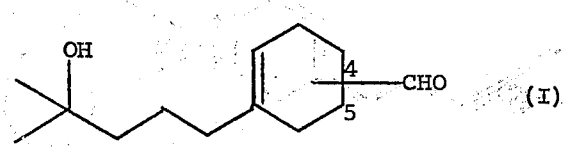

wherein the formyl residue is present in the 4- or 5-position,
or mixtures of the 4- and 5-position isomers of the formula I.

The process is characterised in that an aminal of the formula

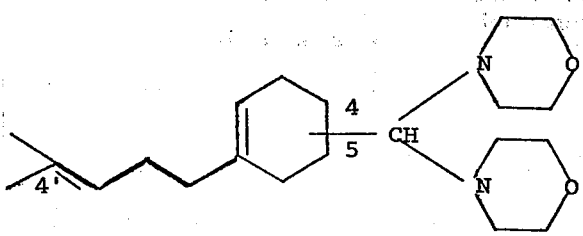

wherein the dimorpholinomethyl residue is present in 4- or 5-position,
or mixtures of the 4- and 5-position isomers of the formula II is/are hydrated to the corresponding 4'-hydroxy compound and the dimorpholino protecting group sebsequently cleaved off.

DESCRIPTION OF THE PREFERRED EMBODIMENTS

The hydration of an aminal of formula II or an aforementioned isomer mixture thereof can be carried out according to methods known per se; for example, by treatment with a non-oxidising mineral acid such as sulphuric acid, phosphoric acid or hydrochloric acid. In order to obtain high yields of the desired product, these mineral acids are expediently used in a relatively concentrated form (e.g. ca 50–70% sulphuric acid, ca 60–70% phosphoric acid or ca 28–33% hydrochloric acid).

The hydration can be carried out at temperature of from approximately −20°C to +30°C, preferably at approximately 0°C to approximately +20°C.

The cleavage of the dimorpholino protecting group can be carried out according to methods known per se, expediently by adjusting the pH-value of the hydration mixture to approximately 7. An aqueous alkali hydroxide solution (e.g. sodium hydroxide) can be used for this purpose. The cleavage of the dimorpholino protecting group is expediently carried out at a slightly elevated temperature (e.g. between approximately 30°C and 35°C). The presence of a water-immiscible organic solvent (e.g. methylene chloride, ethylene chloride, benzene, toluene, etc) is expedient.

The aminals of formula II or mixtures of the 4- and 5-position isomers thereof can be prepared by reacting a compound of the formula

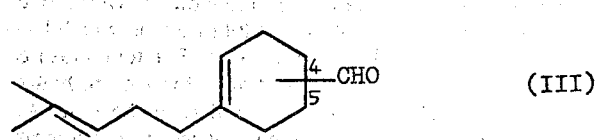

wherein the formyl group is present in the 4- or 5-position,
or a mixture of the 4- and 5-position isomers of formula III, with an excess of morpholine.

In the foregoing reaction, the morpholine is expediently used in at least a 10% excess, preferably in at least a 50% excess.

The reaction is preferably carried out at a temperature between approximately +20°C and +30°C.

The aldehydes of formula I and mixtures of the 4- and 5-position isomers of formula I are known and useful odorants. Accordingly they have diverse applications in the perfume industry; see, for example, S. Arctander, Perfume and Flavor Chemicals I, 1754 (Montclair, N.J. 1969).

The pure isomers can be obtained from the isomer mixture by distillation, e.g. on a spinning band column. Separation is, however, not necessary.

The aminals of formula II and their isomer mixtures aforesaid are novel and also form part of the present invention.

In the following Example the temperatures are given in degrees Celsius.

EXAMPLE 261 g (3 mol) of morpholine are added to a 3-necked flask provided with a stirrer, thermometer and dropping funnel. During 45 minutes there are added dropwise to this mixture at a temperature of 25–30° 127 192 g (1 mol) of a mixture of 65 parts by weight of 4-(4-methyl-3-pentenyl)-Δ³-cyclohexene-carbaldehyde and 35 parts by weight of 3-(4-methyl-3-pentenyl)-Δ³-cyclohexene-carbaldehyde. After the addition, the mixture is further stirred for one hour at 25°–30°. The water formed and the excess morpholine are distilled off at 25°–30°/1 mm Hg from the aminals formed, which was a mixture of 65 parts by weight of 1-dimorpholinomethyl-4-(4-methyl-3-pentenyl)-Δ³-cyclohexene and 35 parts by weight of 1-dimorpholinomethyl-3-

(4-methyl-3-pentenyl)-Δ³-cyclohexene. The yield of the aminals mixture amounted to 352 grams.

Physical data of aminals mixture: $n_D^{20} = 1,5129$; $d^{20} = 1,0241$; IR (n° 25748) 1670 %⁻¹ (weak) trisubstituted double bonds; 1120 cm⁻¹ (strong) C-O-C; 1735 cm⁻¹ no absorption = no carbonyl; NMR (n° 29900) determined in CDCl₃ with Si(CH₃)₄ as internal standard on a Varian EM-360 60 MHz NMR spectrometer; [δ, ppm]: 1,63 (3 H, s, CH₃-C); 1,72 (3 H, s, CH₃-C); 2,02 (8 H, broad s, -CH₂-CH=); 2,82 (9 H, m, -CH₂-N,

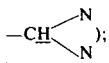

3,70 (8 H, m, -CH₂-O); 5,17 (1 H, t, -CH₂-CH=C<); 5,47 (1 H, broad s, CH₂-C<u>H</u>=C< in cyclohexene).

The resulting aminals mixture and 445 g of 60% sulphuric acid are added simultaneously within one hour at −10° to 345 g of 50% sulphuric acid which has been cooled to −10° in a 4 liter flask. The temperature is held first for 17 hours at 0°, finally for 2 more hours at +10°. 200 ml of toluene are added to the reaction mixture and this is precisely neutralised at a temperature of −10° with 2.4 liter of 10% aqueous sodium hydroxide. After the addition of a further 200 ml of toluene, the reaction mixture is warmed to 30°–35° and stirred at this temperature for 6 hours. The organic layer is then separated and the aqueous phase extracted twice with 200 ml of toluene each time. The toluene extracts are first washed twice with 200 ml of 5% sulphuric acid each time, then to neutrality with water. After distilling off the toluene, there are obtained 193 g of crude product from which there are obtained by double distillation 107 g (51%) of a mixture of 65 parts by weight of 4-(4-methyl-4-hydroxypentyl)-Δ³-cyclohexene-carbaldehyde and 35 parts by weight of 3-(4-methyl-4-hydroxypentyl)-Δ³-cyclohexene-carbaldehyde.

What is claimed is:

1. A compound of the formula:

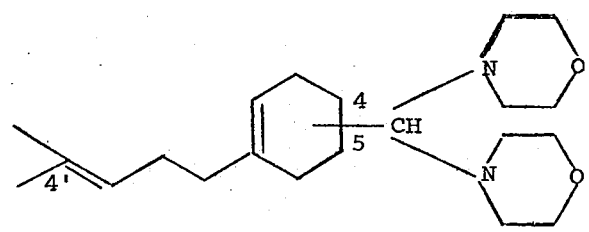

II wherein the dimorpholinomethyl residue is present in the 4- or 5-position,
or mixtures of the 4- and 5-position isomers of the formula II.

* * * * *

UNITED STATES PATENT OFFICE
CERTIFICATE OF CORRECTION

Patent No. 3,935,205          Dated January 27, 1976

Inventor(s) Paul Ochsner

It is certified that error appears in the above-identified patent and that said Letters Patent are hereby corrected as shown below:

Column 2, line 58, remove "127" after "25-30°", should read -- 25-30° 192 ... --.

Signed and Sealed this fourth Day of May 1976

[SEAL]

Attest:

RUTH C. MASON
*Attesting Officer*

C. MARSHALL DANN
*Commissioner of Patents and Trademarks*